United States Patent [19]
Leclerc et al.

[11] Patent Number: 5,821,354
[45] Date of Patent: Oct. 13, 1998

[54] RADIOLABELED DNA OLIGONUCLEOTIDE AND METHOD OF PREPARATION

[75] Inventors: Guy Leclerc, Rosemère; Rémi Martel, Montréal, both of Canada

[73] Assignees: Angiogene Inc.; Centre de Recherche du Centre Hospitalier de l'Universite de Montreal, both of Quebec, Canada

[21] Appl. No.: 756,728

[22] Filed: Nov. 26, 1996

[51] Int. Cl.$^6$ .......................... C07H 21/00; C07H 21/04; A61K 31/70; C12N 5/10

[52] U.S. Cl. .............................. 536/24.5; 435/6; 435/375; 514/44; 536/24.3; 536/24.31; 536/25.32

[58] Field of Search ................................ 435/6, 91.1, 91.2, 435/91.5, 91.52, 325, 375; 514/44; 536/23.1, 24.3, 24.31, 24.5, 25.3, 25.32; 935/33, 34, 36; 424/1.73, 1.77, 1.53

[56] References Cited

U.S. PATENT DOCUMENTS

| | | | |
|---|---|---|---|
| 5,059,166 | 10/1991 | Fischell et al. | 600/3 |
| 5,176,617 | 1/1993 | Fischell et al. | 600/3 |
| 5,494,810 | 2/1996 | Barany et al. | 435/91.52 |
| 5,585,479 | 12/1996 | Hoke et al. | 536/24.5 |

OTHER PUBLICATIONS

"Antisense '97: A roundtable on the state of the industry" Nature Biotechnology 15: 519–524, Jun. 1997.

Gewirtz et al. "Facilitating oligonucleotide delivery: Helping antisense deliver on its promise" Proc. Natl. Acad. Sci. USA 93: 3161–3163, Apr. 1996.

Gura "Antisense has growing pains" Science 270: 575–577, Oct. 1995.

Kang et al. "Pharmokinetics and organ clearance of a 3'–biotinylated, internally [32P]–labeled phosphodiester oligodeoxynucleotide coupled to a neutral aviding/monoclonal antibody conjugate" Drug Metabolism and Disposition 23(1): 55–59, Jan. 1995.

Milligan et al. "Current concepts in antisense drug design", J. Med. Chem. 36(14): 1923–1937, Jul. 1993.

Rigby et al. "Labeling deoxyribonucleic acid to high specific activity in vitro by nick translation with DNA polymerase I" J. Mol. Biol. 113: 237–251, 1977.

Stull et al. Antigene, ribozyme and aptamer nucleic acid drugs: Progress and prospects. Pharm. Res. 12(4): 465–483, Apr. 1995.

Rivard A et al., 1996, *Circulation*, 94(8):210.
Verin et al., 1995, *Circulation*, 92:2284–2290.
Waksman R. et al., 1995, *Circulation*, 91:1533–1539.
Waksman R. et al., 1995, *Circulation*, 92:1383–1386.

*Primary Examiner*—Nancy Degen
*Assistant Examiner*—Thomas G. Larson
*Attorney, Agent, or Firm*—Klauber & Jackson

[57] ABSTRACT

The present invention relates to a radiolabeled DNA oligonucleotide, a method of preparation thereof and the therapeutic uses of this substance to prevent uncontrolled cellular proliferation. The invention also relates to devices incorporating the above radiolabeled DNA oligonucleotide for the therapeutic treatment of uncontrolled cellular proliferation. More specifically, the present invention is concerned with the prevention of restenosis by coronary delivery of radiolabeled DNA oligonucleotide at a dilatation site of an artery. This invention is also directed to a method of treatment of vascular proliferative diseases and/or other proliferative disorders such as cancer and related metastasis. More particularly, the invention relates to the preparation of DNA sequences carrying one or several radioisotopes, located within the DNA sequence, and which are able to prevent cell proliferation in vitro and, pursuant to local drug delivery, are able to prevent cell proliferation in vivo, more particularly restenosis and malignant tumors. In other words, the invention relates to the synthesis process, the stability data of the radiolabeled DNA oligonucleotide, the efficacy of the invention in vitro, in cell culture, and the in vivo delivery of the molecule.

14 Claims, 2 Drawing Sheets

Antisense synthesized in 2 parts

5' A-A-A-A-A-A-A 3'   5' A-A-A-A-A-A-A-A 3'

Label 5' end of one sequence

32P-ATP + 5' A-A-A-A-A-A-A-A 3' → 5' A-A-A-A-A-A-A-A 3'
                                              *

Anneal both parts to sense sequence

5' T-T-T-T-T-T-T-T-T-T-T-T-T-T-T-T-T-T 3'
         3' A-A-A-A-A-A-A-A  A-A-A-A-A-A-A 5'
                             *

Ligate the 2 parts of the antisense

5' T-T-T-T-T-T-T-T-T-T-T-T-T-T-T-T-T-T 3'
         3' A-A-A-A-A-A-A-A-A-A-A-A-A-A-A 5'
                             *

Separate the 2 strands and purify the antisense

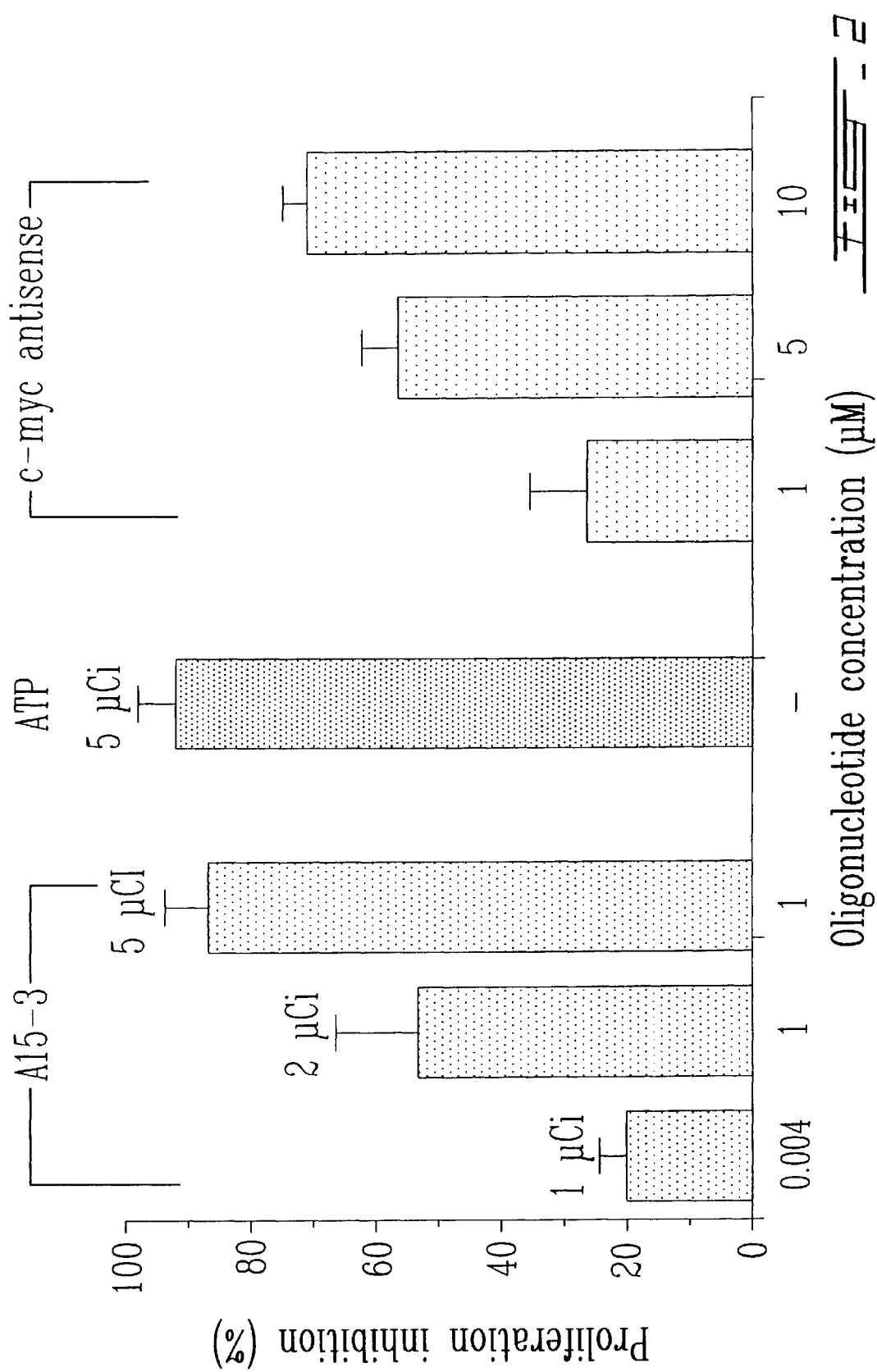

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:

(A) LENGTH: 19 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "PRIMER"

(iii) HYPOTHETICAL: NO (xi) SEQUENCE DESCRIPTION: SEQ ID NO:1:

TTTTTTTTT TTTTTTTT    19

(2) INFORMATION FOR SEQ ID NO:2:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "PRIMER"

(iii) HYPOTHETICAL: NO (xi) SEQUENCE DESCRIPTION: SEQ ID NO:2:

AAAAAAAAA AAAAA    15

(2) INFORMATION FOR SEQ ID NO:3:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "cmyc"

(iii) HYPOTHETICAL: NO (xi) SEQUENCE DESCRIPTION: SEQ ID NO:3:

CACGTTGAGG GGCAT    15

(2) INFORMATION FOR SEQ ID NO:4:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "FOS"

(iii) HYPOTHETICAL: NO (xi) SEQUENCE DESCRIPTION: SEQ ID NO:4:

GCCCGAGAAC ATCAT    15

(2) INFORMATION FOR SEQ ID NO:5:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Jun"

-continued (iii) HYPOTHETICAL: NO (xi) SEQUENCE DESCRIPTION: SEQ ID NO:5:

CCTCGCAGTT TCCAT                                                                                    15

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "c- mycl9"

(iii) HYPOTHETICAL: NO (xi) SEQUENCE DESCRIPTION: SEQ ID NO:6:

ATGCCCCTCA ACGTGAAAA                                                                                19

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO:7:

CACGTTGAGG GGCAT                                                                                    15

RADIOLABELED DNA OLIGONUCLEOTIDE AND METHOD OF PREPARATION

BACKGROUND OF THE INVENTION (a) Field of the Invention

The invention relates to a radiolabeled DNA oligonucleotide, a method of preparation thereof and the therapeutic uses of this substance to prevent uncontrolled cellular proliferation. The invention also relates to devices incorporating the above radiolabeled DNA oligonucleotide for the therapeutic treatment of uncontrolled cellular proliferation. More specifically, the present invention is concerned with the prevention of restenosis by coronary delivery of radiolabeled DNA oligonucleotide at a dilatation site of an artery. This invention is also directed to a method of treatment of vascular proliferative diseases and/or other proliferative disorders such as cancer and related metastasis. More particularly, the invention relates to the preparation of DNA sequences carrying one or several radioisotopes, located within the DNA sequence, and which are able to prevent cell proliferation in vitro and, pursuant to local drug delivery, are able to prevent cell proliferation in vivo, more particularly restenosis and malignant tumors. In other words, the invention relates to the synthesis process, the stability data of the radiolabeled DNA oligonucleotide, the efficacy of the invention in vitro, in cell culture, and the in vivo delivery of the molecule.

(b) Description of Prior Art

Despite the favorable impact of balloon angioplasty on the non-surgical treatment of coronary and peripheral vascular disease, this otherwise invaluable intervention remains plagued by a high incidence of restenosis that has resisted all pharmacological attempts to prevent it. Proliferation of vascular smooth muscle cells is considered to represent the fundamental process underlying restenosis. Low dose endovascular irradiation, either catheter or stent based, was recently proposed to be used following balloon angioplasty as it is recognized that ionizing radiation may be effective in inhibiting exuberant wound healing responses in various clinical situations. Radiation emitted from a $^{192}$iridium source (beta and gamma emission), a $^{90}$yttrium source, or a $^{90}$strontium/yttrium source (both pure beta emitters) introduced for a short period of time via a catheter system and immediately removed after angioplasty inhibited subsequent intimal hyperplasia in a pig model of restenosis. Similar results were recently obtained, in applicant's laboratory, using radioactive, $^{32}$p ion implanted stents in coronary arteries (Rivard A et al., 1996, *Circulation*, 94(8):210). It was suggested that radiation originating from the beta-emitting wires may have inhibited hyperplasia by either killing progenitor cells or by limiting their replicative capacity. Therapies based on 32 phosphorus systemic injections are currently used to treat diseases such as polycythemia vera, chronic myelocytic and lymphocytic leukemias and skeletal metastases of various origins.

Percutaneous transluminal angioplasty is an accepted form of treatment of coronary and peripheral vascular disease. Since its introduction in 1977 for the treatment for coronary disease, primary success rates have reached very high levels (90% to 95%) and complication rates of 1% to 5% are now the standards. But it was observed that in a certain percentage of patients treated by balloon angioplasty the narrowing treated would reoccur at the same site within three to six months. Angiographic studies indicate that the incidence of restenosis following successful balloon angioplasty may be as high as 55% and 65% in the coronary and peripheral arteries respectively. All pharmacological approaches to prevent the occurrence of restenosis have failed. A number of mechanical alternatives to balloon angioplasty have been developed and investigated, and none has yet been shown to diminish conclusively the incidence of restenosis following percutaneous revascularization, except for a modest reduction obtained with the Palmaz-Schatz stent in selected patients. This effect is explained by the propensity of the stent to achieve a consistently greater increase in lumen diameter immediately after the procedure by limiting the phenomenon of elastic recoil. Although many of the risk factors for restenosis have been identified, most of them are difficult to influence.

Percutaneous transluminal angioplasty results in unavoidable vessel wall injury. Disruption of endothelial and vessel wall structure triggers molecular and cellular events which leads in some patients to restenosis. Several growth factors, cytokines and cell-surface receptors have been implicated in this proliferation process. In animal models of vascular injury, following the immediate loss of lumen diameter accounted by elastic recoil, an important cascade of events leads to smooth muscle cell (SMC) proliferation that begins 24 hours post-angioplasty. SMC proliferation appears to be a consistent response to balloon dilatation and/or denudation of the artery. Cell replication has been reported to peak within seven days after the angioplasty; and twenty-eight days after the angioplasty, SMC proliferation in the media as well as in the intima appears normalized. This process is then followed by matrix deposition over the next several weeks.

The same problems are faced in the treatment of localized cancerous tumors where it has been found impossible to achieve a successful localized radiation treatment.

Recent studies have indicated that restenosis rates in animal models can be reduced by intra-coronary radiotherapy (ICRT) during or after angioplasty with or without the application of a stent. Early experiments with low level radioactive stainless steel stents implanted in rabbits indicated a complete inhibition of neointimal cell proliferation (U.S. Pat. Nos. 5,059,166 and 5,176,617). Inhibition of neointimal proliferation has also been recently reported in swine experiments using 14 titanium stents, 7 of which were heavily implanted with $^{32}$p and neutron activated to produce low dose true beta particle emitting isotope phosphorus 32 ($^{32}$p).

Intracoronary irradiation with $^{192}$Ir ribbons has also been reported to markedly reduce neointima formation in swines. $^{192}$Ir decays via negative beta emission with a maximum energy of 0.67 MeV and primary gamma emission in the energy range of 0.3–0.6 MeV. The half life is 74.2 days. It is used primarily in brachytherapy where the radioactive source is placed directly into a tumor or at the extirpation site to deliver a given treatment dose and then is removed. This benefit appeared to be sustained at 6 months, with no evidence of late radiation sequelae.

Waksman reported their experience with a high activity $^{192}$Ir source introduced into a pig coronary arteries after the injury was created (Waksman R. et al., 1995, *Circulation*, 91:1533–1539). They showed that the intimal area-to-medial fracture length was inversely correlated with the different radiation doses, with a significant reduction in neointimal formation at all doses when compared to control arteries. A report of stent implantation combined with $^{192}$Ir ribbon radiation dose delivery also indicated a net reduction of neointima formation in pig coronary arteries.

Finally, the use of a wire or catheter with a pure beta emitter ($^{90}$yttrium source), ($^{90}$Strontium/Yttrium source), was reported (Verin et al., 1995, *Circulation*, 92:2284–2290; Waksman R. et al., 1995, *Circulation*, 92:1383–1386). A dose-response relation was demonstrated, without further inhibitory effect at doses beyond 28 Gy.

Recently, precision dose of radiation therapy was delivered percutaneously into the human coronary artery in 10 patients. An Iridium-192 source wire was after loaded through a coronary catheter system and a treatment dose of 2 000 cGy was delivered to the intima of each coronary artery segment with treatment times ranging from 5 to 15 minutes. No angiographic control data at 6 month was reported. From this study, it was concluded that percutaneous transluminal coronary angioplasty (PTCA)-ICRT can be delivered safely to humans, but the efficacy of ICRT in reducing coronary restenosis in the test population remains to be asserted.

All of these results are very encouraging and suggest that a significant reduction in the rate of restenosis may be obtained by ICRT following PTCA. However, there is currently no consensus on the ideal radioactive source, the dose delivery level and method to be used.

It would be highly desirable to be able to effect radiotherapy from within the target tissue itself instead of extratissular exposure. This may result in a more efficient strategy to prevent restenosis and potentially any other vascular proliferative disease or/and treat other proliferative processes such as cancer and related metastasis.

SUMMARY OF THE INVENTION

With the recent development of site-specific drug delivery for vascular disease, according to the present invention, beta irradiation of the angioplasty site through molecular radiotherapy by delivering phosphorus 32 locally through a labeled DNA oligonucleotide at the dilatation site appears feasible and prevents smooth muscle cell proliferation and restenosis.

The present invention may be combined with other therapeutic modalities that have been shown efficient in arteries such as stenting. This local drug delivery strategy based on the use of the invention presented here may be applicable to all vascular proliferative disorders such as coronary and peripheral arterial restenosis, arterio venous fistulas, etc. and cancer and metastasis therapy.

It is therefore an object of the present invention to provide a new and innovative approach to prevent restenosis and potentially any other vascular proliferative disease or/and treat other proliferative processes such as cancer and related metastasis.

It is another object of the present invention to provide short DNA sequences that carry one or several radioisotopes, located internally within the DNA sequence, and which are able to prevent cell proliferation in vitro and, following local drug delivery to prevent the occurrence of restenosis in vivo.

Other objects of the invention will appear as the description follows.

In accordance with the present invention, there is provided a therapeutic substance comprising a radiolabeled DNA oligonucleotide, wherein the radioisotope is located internally within the DNA sequence.

The radioisotope used to radiolabel the oligonucleotide of the present invention may be an alpha, beta or gamma emitter. Preferred radioisotopes in accordance with the present invention include, without limitation, $^{32}P$, $^{33}P$, $^{125}I$, $^{35}S$, $^{198}AU$, $^{90}Y$, $^{89}SR$, $^{186}Re$, and $^{153}Sm$ among others. The half-life of the preferred radioisotopes used in accordance with the present invention should vary between 10 hours and 1000 days.

The oligonucleotide is a double-stranded DNA sequence or a single-stranded DNA sequence.

In accordance with another preferred embodiment, the oligonucleotide sequence is a sense or antisense sequence.

In accordance with a preferred embodiment, the oligonucleotide is conjugated with an antibody for cell-specific delivery of the oligonucleotide.

In accordance with another preferred embodiment, the oligonucleotide is conjugated to a lipid moiety, such as cholesterol, to favorably influence its pharmacokinetic properties.

The radiolabeled oligonucleotide of the present invention may be directly or indirectly attached to a stent surface to prevent uncontrolled cellular proliferation occurring in cases of restenosis.

Preferably, any sequences of DNA of at least about 2 nucleotides to about 5000 nucleotides may be used as a DNA oligonucleotide in accordance with the present invention, preferably a DNA sequence of less than 20 nucleotides. For example the following sequences may be used:

| cmyc | CAC GTT GA*G GGG CAT | (SEQ ID NO:3) |
|------|----------------------|---------------|
| FOS  | GCC CGA* GAA CAT CAT | (SEQ ID NO:4) |
| Jun  | CCT CGC* AGT TTC CAT | (SEQ ID NO:5) | wherein * indicates the position of a radioisotope, such as $^{32}P$, wherein the radioisotope may be located at any position in the underlined region.

The invention also relates to a method for preparing a radiolabeled DNA oligonucleotide sequence wherein the radioisotope is located internally within the DNA sequence, which comprises the steps of:

a) synthesizing a DNA sequence in at least two parts;

b) labeling the 5' end of one of the two parts with a radioisotope;

c) hybridizing the two or more parts of step b) with a sequence capable of hybridizing under stringent conditions; and d) ligating together the hybridized two or more parts to form a radiolabeled double-stranded DNA oligonucleotide.

In order to obtain a radiolabeled single-stranded oligonucleotide, the method further includes a step e) after above step d), which comprises e) separating the hybridized DNA and recovering the radiolabeled single-stranded DNA oligonucleotide sequence.

Also, when a double-stranded oligonucleotide having both strand radiolabeled is desired, the method further includes a step f) after above step e), which comprises f) hybridizing together complementary radiolabeled single-stranded DNA oligonucleotides of step e).

When the two parts of step a) form an antisense sequence, the sequence capable of hybridizing of step c) is a corresponding sense sequence.

When the two parts of step a) form a sense sequence, the sequence capable of hybridizing of step c) is a corresponding antisense sequence.

The invention further relates to a method for the prevention of uncontrolled cell proliferation in a mammal, which comprises delivering a therapeutic substance as defined above to the mammal in situ where the uncontrolled cell proliferation takes place. For example, when the uncontrolled cell proliferation is a restenosis following angioplasty, therapeutic substance is delivered by site-specific coronary delivery.

Another possibility is when the uncontrolled proliferation is cancer or a malignant tumor. For this case, the therapeutic substance is coupled to an antibody or a peptide moiety. Such a peptide moiety include, without limitation, Transforming Growth Factor α(TGFα), TGFβ, cytokines and any growth factors. The coupled radiolabeled oligonucleotide may be given locally, in a site specific manner, or systemically.

This therapeutic, internally-radiolabeled oligonucleotide may be conjugated to other moieties, such as cholesterol, oleic acid or linoleic acid, to favorably influence its vascular pharmacokinetic properties. It may also be conjugated with an antibody to increase its cell specificity. The DNA sequence, which solely acts as a radioisotope carrier may be a sense or antisense sequence to a known genetic target. The sequence used does not represent the therapeutic portion of the molecule. The anti-proliferative activity of the molecule stems from the radioactive isotope attached to the DNA.

BRIEF DESCRIPTION OF THE DRAWINGS

FIG. 1 is a schematic representation of a $^{32}$P-labeled antisense DNA sequence in accordance with one embodiment of the present invention SEQ. ID. NOS.: 1 and 2; and FIG. 2 is a graph of the effect of $^{32}$P-labeled (A15-3), SEQ. ID. NO.: 3 oligonucleotide of the present invention and unlabeled c-myc antisense on smooth muscle cells proliferation.

DETAILED DESCRIPTION OF THE INVENTION

Most of the approaches with $^{32}$P described previously are related to a source remaining external to the target cells, are already patented, and several, namely the stent-based approach, would be very difficult to implement in daily practice for practical reasons. Applicants have gained an important expertise in the field of local drug delivery, namely that of antisense DNA to prevent restenosis. Two technologies, that of a beta-emitting source and DNA antisense, to effect the prevention of restenosis, were combined in a unique and original way.

The preferred radioisotope in accordance with the present is $^{32}$P, which is a pure beta emitter with an average energy of 0.69 MeV, a maximum energy of 1.71 MeV (maximum range of ~8 mm in soft tissues) and a half life of 14.3 days. Using an efficient tissue carrier for $^{32}$P has enabled to effect the radiotherapy from within the vessel wall and potentially within cells.

In accordance with the present invention, an antisense oligonucleotide directed against the proto-oncogene c-myc was used to demonstrate the potential of a radiolabeled ($^{32}$P-labeled) oligonucleotide to inhibit proliferation of cells.

End labeling of oligonucleotides with a radioiosotope ($^{32}$P) is a very common reaction in molecular biology. However, this end labeling is more difficult to achieve with phosphorothioate as compared to phosphodiester oligonucleotides. Furthermore, phosphodiester oligonucleotides are readily degraded in vivo (within hours) by nucleases after transfection. The labeling of the 5' end or the 3'end of an oligonucleotide does not exhibit a strong stability and the label could be cleaved from the oligonucleotide once it is incubated with cells. A method to label the oligonucleotide in an internal position was used. The schematic representation of the method of preparing such a radiolabeled oligonucleotide is outlined in FIG. 1.

The sequence of the final product used to perform this demonstration is: CACGTTGA(*)GGGGCAT SEQ. ID. NO.: 7 (the * indicates the position of the radioactive phosphorus atom). To achieve this result, the following three (3) different oligonucleotides of Table 1 below were used.

TABLE 1

| Oligonucleotide | Sequence | Characteristic |
|---|---|---|
| 1. c-myc19 | ATGCCCCTCAACGTGAAAA (SEQ. ID. NO: 6) | phosphorothioate or phosphodiester |
| 2. c-my1 | CACGTTGA | phosphorothioate |
| 3. c-myc12 | GGGGCAT | phosphorothioate-phosphodiester |

The third oligonucleotide (c-myc2) is a mixed phosphorothioate-phosphodiester molecule. The first 2 internucleotide bounds are phosphodiester while the remaining bounds are phosphorothioates. The synthesis of the internally labeled oligonucleotide involves the 5' end labeling of c-myc2 followed by the annealing of c-myc2 and c-myc1 to c-myc19, then by the ligation of c-myc2 to c-myc1, and finally by the separation of c-myc2-c-myc1 from c-myc19.

The first reaction is the labeling of the c-myc2 oligonucleotide at the 5' end. The labeling is achieved by incubating between 50 and 100 pmole of the oligonucleotide with 50 μCi of g$^{32}$P-ATP and 2 units of T4 polynucleotide kinase at 37° C. for 2×30 minutes (a second input of the kinase is made after the first 30 minutes). The unincorporated $^{32}$P is removed from the mix by gel filtration.

For the annealing the $^{32}$P labeled c-myc2 is recovered and incubated with equimolar quantities of c-myc19 and c-myc1 for 30 minutes at 550° C. in presence of 12.5 mM TRIS-HCl (pH 8.5), 12.5 mM MgCl$_2$, and then cooled to room temperature.

The ligation of c-myc2 to c-myc1 is done by incubating the annealing mix overnight at 16° C. in the presence of 33 mM CH$_3$COOK, 1 mM ATP, and 14 units of T4 DNA ligase.

To separate the ligated c-myc2-c-myc1 from the c-myc19, an equal volume of formamide buffer (80% formamide, 10 mM EDTA, 1 mg/ml bromophenol blue, xylene cyanol) is added to the ligation mix, the sample is then heated 5 minutes at 65° C. and then loaded on a 20% polyacrylamide-urea gel for electrophoresis. After migration, the band corresponding to the ligated c-myc2-c-myc1 (15 bases long) is cut from the gel. The cut piece of gel is crushed in a fine powder and the powder is incubated with 2 volumes of TE (10 mM TRIS-HCL (pH 7.5), 1 mM EDTA) for 30 minutes at 55° C. The eluate is recovered after centrifugation and desalting is achieved by affinity chromatography. Using this method it was possible to produce an internally $^{32}$P-labeled oligonucleotide. The activity of the recovered oligonucleotide was of the order of 1.2 μCi.

The synthesis of all oligonucleotides is carried out in an oligonucleotide synthesizer which is sold by Applied Biosystems under the designation 392 DNA/RNA Synthesizer™. After synthesis, the oligonucleotides are purified in Poly-Pak™ II columns bought from Glen Research. Alternatively, they can be purified by HPLC (High Pressure Liquid Chromatography).

A15-3 is another name for the antisense c-myc containing an internal $^{32}$P. A is the antisense and 15-3 means that the oligonucleotide is 15 bases long and contains 3 phosphodiesters bonds (all the other internucleotide bonds being phosphorothioates bonds).

The non radioactive antisense c-myc contains phosphorothioate bonds between each nucleotide.

ATP represents adenosine 5'-triphosphate (triethylammonium) salt, [γ-$^{32}$P] bought from DuPont, catalogue No. NEG-002A.

The effect of this internally $^{32}$P-labeled oligonucleotide was verified on smooth muscle cell growth. To measure proliferation of smooth muscle cell the tritiated thymidine incorporation assay was used. The cells are made quiescent by incubating them in a starvation medium. Proliferation is activated by increasing the bovine fetal serum content of the medium. The labeled oligonucleotide was added to the cells in quadruplet wells at the time of the activation. Tritiated thymidine was added to medium 12 hours after the activation and determination of the incorporation of the tritiated thymidine by the cells was determined after a further incubation of 12 hours. Stability of the $^{32}$P-labeled oligonucleotide was also assessed by incubating a dose of 0.2 μCi of the oligonucleotide in the presence of smooth muscle cells. After an incubation of 7 days, the integrity of the $^{32}$P-labeled oligonucleotide was confirmed by polyacrylamide-urea gel electrophoresis.

First the potential use of $^{32}$P-irradiation in vitro was evaluated by incorporating $^{32}$P-labeled ATP in proliferating vascular smooth muscle cells. The effect of irradiation on cellular proliferation was evaluated by thymidine incorporation index. Different doses of alpha-$^{32}$P ATP (0.5, 1, or 5 μCi) were added to the cultured cells at the activation time. The results indicate proliferation inhibition of 26%, 41%, and 95% respectively for the 0.5, 1, and 5 μCi doses. Although these experiments clearly demonstrate the potential of this approach, it was sought to develop a strategy that would enable to keep the radioactive molecule in the vessel wall for a sustained period of time.

Indeed, data obtained has clearly shown that simply transfecting the labeled ATP into vascular smooth muscle cells resulted in a rapid washout of the labeled ATP from the cells, thus rendering the therapy less prone to achieve the inhibition of a proliferative process that takes place over several days. The strategy of carrying the radioactivity into the cells by labeling DNA oligonucleotides with $^{32}$P was then evaluated.

Phosphorothioate oligonucleotides have proved to be very good candidates to achieve this goal since their stability after transfection has been demonstrated for a period of at least 7 days. The results confirmed the feasibility of this approach. In vitro data shows that:

radiolabeled ($^{32}$P) oligonucleotides achieve a dose-dependent inhibition of smooth muscle cell proliferation;

this inhibition level often reaches 100% at a dose of 5 μCi of labeled DNA;

high efficiency inhibition is not dependent on the sequence of the DNA but on the radioactivity level given to the cells;

over the course of a short-term administration (12 hours), the inhibition level for 5 μCi of either labeled ATP and labeled DNA are the same;

labeled ATP rapidly comes out of the cell following transfection and thus would represent a second choice of in vivo therapy compared to labeled DNA;

the level of inhibition of smooth muscle cell proliferation obtained with radiolabeled ($^{32}$P) oligonucleotide is greatly superior (from 4 to 20 times higher) to that obtained with non radioactive identical DNA sequences, for the same amount of DNA used, as shown in FIG. 2;

a maximal inhibition level has been attained with radiolabeled ($^{32}$P) oligonucleotide (100% inhibition at 5 μCi) whereas this inhibition level has never been observed with conventional oligonucleotides; and an exposure-dependent effect is observed with the radiolabeled ($^{32}$P) oligonucleotide, with an increasing proliferation inhibition effect as continuous exposure of cells to radiolabeled ($^{32}$P) oligonucleotide increases.

Based on these data and the demonstration of the feasibility to locally deliver the radiolabeled ($^{32}$P) oligonucleotides at the site of angioplasty, it is reasonable to infer that in vivo prevention of smooth muscle cell proliferation is expected following local delivery of radiolabeled ($^{32}$P) oligonucleotides. This local, site-specific, delivery can be performed in coronary arteries by using local drug delivery catheters that are commercially available, such as the "Dispatch" or "Transport" catheter.

The above method of radiolabeling antisense nucleotides with $^{32}$P in such a way to prevent its degradation by nuclease enzymes can also be applied to the field of oncology, thereby providing a mean for the specific delivery of therapeutically effective radiation dose to the tumor while minimizing normal tissue exposure.

This can be achieved for example by first radiolabeling an antisense DNA sequence that has an high affinity with cancer cells genetic material. Then the radiolabeled antisense sequence is bonded to a monoclonal antibody (MoAb) which recognizes tumor associated antigens. Such a bond between the radiolabeled antisense and the MoAb can be done through an aminolink with the use of "Peptide Nucleic Acids" (PNA's) specifically designed for that purpose.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

We claim:

1. An anti-proliferative substance for preventing uncontrolled cellular proliferation, which comprises a radiolabeled DNA oligonucleotide selected from the group consisting of CAC GTT GAG GGG CAT  (SEQ ID NO:3);
    GCC CGA GAA CAT CAT  (SEQ ID NO:4); and
    CCT CGC AGT TTC CAT  (SEQ ID NO:5);

wherein a radioisotope is located internally within the DNA sequence at any position between nucleotide 4 and 12.

2. The anti-proliferative substance according to claim 1, wherein said radioisotope is selected from the group consisting of $^{32}P$, $^{33}P$, $^{125}I$, $^{35}S$, $^{198}AU$, $^{90}Y$, $^{89}SR$, $^{186}Re$ and $^{153}Sm$.

3. The anti-proliferative substance according to claim 1, wherein said oligonucleotide is a double-stranded DNA sequence or a single-stranded DNA sequence.

4. The anti-proliferative substance according to claim 1, wherein said oligonucleotide is conjugated with an antibody for cell-specific delivery.

5. The anti-proliferative substance according to claim 3, wherein said DNA oligonucleotide sequence is a single-stranded sense DNA sequence for hybridization to a specific genetic target.

6. The anti-proliferative substance according to claim 3, wherein said DNA oligonucleotide sequence is a single-stranded antisense DNA sequence for hybridization to a specific genetic target.

7. The anti-proliferative substance according to claim 1, wherein the oligonucleotide is conjugated to at least one selected from the group consisting of a stent surface, cholesterol, oleic acid, linoleic acid, TGFα, antibody, TBFβ, cytokines, and growth factors.

8. The anti-proliferative substance according to claim 7, wherein the radioisotope is selected from the group consisting of $^{32}P$, $^{33}P$, $^{125}I$, $^{35}S$, $^{198}AU$, $^{90}Y$, $^{89}SR$, $^{186}Re$, and $^{153}Sm$.

9. A method for preparing a radiolabeled DNA oligonucleotide sequence selected from the group consisting of CAC GTT GAG GGG CAT  (SEQ ID NO:3);
    GCC CGA GAA CAT CAT  (SEQ ID NO:4); and
    CCT CGC AGT TTC CAT  (SEQ ID NO:5);

wherein a radioisotope is located internally within the DNA sequence, which comprises the steps of:

a) synthesizing a DNA sequence in at least two parts;

b) labeling the 5' end of one of said two parts with a radioisotope;

c) hybridizing said two parts of step b) with a further sequence; and d) ligating together said hybridized two parts.

10. The method of claim 9, which further includes a step e) after step d) to obtain a single-stranded radiolabeled DNA oligonucleotide, which comprises:

e) separating the hybridized DNA and recovering the radiolabeled DNA oligonucleotide sequence.

11. The method of claim 10, which further includes a step f) after step e) to obtain a double-stranded having both strand radiolabeled, which comprises:

f) hybridizing together complementary radiolabeled single-stranded DNA oligonucleotides of step e).

12. The method of claim 9, wherein said radioisotope is selected from the group consisting of $P^{32}$, $P^{33}$, $^{125}I$, $^{35}S$, $^{198}AU$, $^{90}Y$, $^{89}SR$, $^{186}Re$, and $^{153}Sm$.

13. The method of claim 9, wherein said two parts of step a) form an antisense sequence and said further sequence of step c) is a corresponding sense sequence.

14. The method of claim 9, wherein said two parts of step a) form a sense sequence and said further sequence of step c) is a corresponding antisense sequence.

* * * * *